(12) United States Patent
Mujtaba et al.

(10) Patent No.: US 9,297,697 B2
(45) Date of Patent: Mar. 29, 2016

(54) IN-DEVICE COEXISTENCE BETWEEN RADIOS

(71) Applicant: Apple Inc., Cupertino, CA (US)

(72) Inventors: Syed A. Mujtaba, Santa Clara, CA (US); William S. Burchill, San Jose, CA (US)

(73) Assignee: Apple Inc., Cupertino, CA (US)

(*) Notice: Subject to any disclaimer, the term of this patent is extended or adjusted under 35 U.S.C. 154(b) by 0 days.

(21) Appl. No.: 13/910,471

(22) Filed: Jun. 5, 2013

(65) Prior Publication Data
US 2013/0324049 A1 Dec. 5, 2013

Related U.S. Application Data

(60) Provisional application No. 61/655,994, filed on Jun. 5, 2012.

(51) Int. Cl.
*H04W 28/04* (2009.01)
*G01J 3/453* (2006.01)
*H04B 15/00* (2006.01)
*G01N 21/3504* (2014.01)

(52) U.S. Cl.
CPC ............ *G01J 3/453* (2013.01); *G01N 21/3504* (2013.01); *H04B 15/00* (2013.01); *G01N 2201/06113* (2013.01)

(58) Field of Classification Search
CPC ...... H04W 28/04; H04B 1/525; H04B 1/1027
USPC ............. 455/63.1, 63.3, 67.11, 67.13, 114.2, 455/522, 41.2
See application file for complete search history.

(56) References Cited

U.S. PATENT DOCUMENTS

| | | | | |
|---|---|---|---|---|
| 7,072,616 B2* | 7/2006 | Godfrey | ........................ | 455/41.2 |
| 7,489,902 B2* | 2/2009 | Amani et al. | ................ | 455/63.1 |
| 7,966,037 B2 | 6/2011 | Rayzman et al. | | |
| 8,040,577 B2* | 10/2011 | Akiyama | ...................... | 358/486 |

(Continued)

FOREIGN PATENT DOCUMENTS

| | | |
|---|---|---|
| TW | 201110577 | 3/2011 |
| TW | 201204071 | 1/2012 |

(Continued)

OTHER PUBLICATIONS

International Search Report and Written Opinion in PCT Application PCT/US2013/055269, dated Oct. 30, 2013.

*Primary Examiner* — Minh D Dao
(74) *Attorney, Agent, or Firm* — Downey Brand LLP

(57) ABSTRACT

A method for facilitating in-device coexistence between radios is provided. The method can include a processor implemented on the wireless communication device defining a coexistence policy for a first radio and a second radio co-located on the wireless communication device; and providing the coexistence policy to a coexistence management controller on the first radio via an interface between the processor and the first radio. The method can further include the second radio providing state information for the second radio to the first radio via an interface between the first radio and the second radio. The method can additionally include the coexistence management controller on the first radio using the state information to control operation of the first radio in accordance with the coexistence policy to mitigate interference with the second radio.

20 Claims, 9 Drawing Sheets

(56) References Cited

U.S. PATENT DOCUMENTS

| | | |
|---|---|---|
| 8,095,176 B2 | 1/2012 | Sudak |
| 8,126,399 B1 * | 2/2012 | Lee ............................. 455/41.2 |
| 8,160,001 B2 | 4/2012 | Bitran |
| 8,165,153 B2 | 4/2012 | Kaidar et al. |
| 8,417,187 B2 | 4/2013 | Chen et al. |
| 8,824,966 B2 * | 9/2014 | Boes ............................ 455/63.1 |
| 2008/0051085 A1 | 2/2008 | Ganton |
| 2009/0081962 A1 * | 3/2009 | Sohrabi ............................ 455/79 |
| 2010/0304685 A1 | 12/2010 | Wietfeldt et al. |
| 2010/0330977 A1 | 12/2010 | Kadous et al. |
| 2011/0026432 A1 | 2/2011 | Gruber et al. |
| 2011/0059768 A1 * | 3/2011 | Pandruvada ............... 455/552.1 |
| 2011/0205986 A1 | 8/2011 | Medapalli |
| 2011/0312288 A1 | 12/2011 | Fu et al. |
| 2012/0155303 A1 | 6/2012 | Kuo |
| 2012/0176923 A1 | 7/2012 | Hsu et al. |
| 2012/0195298 A1 | 8/2012 | Kuo |
| 2012/0213150 A1 | 8/2012 | Oguz et al. |
| 2012/0281563 A1 | 11/2012 | Comsa et al. |

FOREIGN PATENT DOCUMENTS

| | | |
|---|---|---|
| WO | WO2011014360 | 2/2011 |
| WO | WO2011106159 | 9/2011 |
| WO | WO2012061765 | 5/2012 |
| WO | WO2012177622 | 12/2012 |
| WO | WO2013048571 | 4/2013 |

* cited by examiner

IN-DEVICE COEXISTENCE BETWEEN RADIOS

CROSS-REFERENCE TO RELATED APPLICATIONS

This application claims priority to U.S. Provisional Patent Application No. 61/655,994, filed on Jun. 5, 2012, which is incorporated herein in its entirety by reference.

FIELD OF THE DESCRIBED EMBODIMENTS

The described embodiments relate generally to wireless communications and more particularly to facilitating in-device coexistence between radios.

BACKGROUND

Many modern wireless communication devices include multiple radios. These multiple radios may be used by the device to concurrently communicate via multiple wireless communication technologies. In many instances, wireless communication technologies used by a device use channel bands that may interfere with each other. In such instances, energy from a band used by one technology can leak into a band used by another technology. This energy leakage can raise the noise floor and cause a problem known as desense. In many instances, desense can negatively impact the use of certain channel bands and, in severe cases, can render certain channel bands unusable. Accordingly, interference that can result in desense poses a problem for in-device coexistence of multiple radios using disparate wireless communication technologies.

A particularly troublesome desense problem can result in a scenario in which a one radio emits a transmission via a first wireless communication technology, referred to as an aggressor wireless communication technology, or aggressor technology, while another radio receives data via a second wireless communication technology, referred to as a victim wireless communication technology, or victim technology. Data receipt via the victim technology can be damaged by the aggressor transmission, particularly in instances in which the radio using the aggressor technology uses a relatively high transmission power. In this regard, received packet errors, or even complete deafening of the radio using the victim technology receiver can result from the interference that can be caused by the aggressor technology transmission. For example transmission of a cellular signal by a first radio on a device at a time when a Bluetooth or wireless local area network (WLAN) signal is received by a second radio on the device can deafen the second radio, causing errors and, in some cases, loss of connection.

SUMMARY OF THE DESCRIBED EMBODIMENTS

Some embodiments disclosed herein provide an architecture and corresponding methods, apparatuses, and computer program products for facilitating in-device coexistence between radios. For example, some example embodiments facilitate coexistence between a cellular radio and a connectivity radio, such as a connectivity radio using an Industrial, Scientific, and Medical (ISM) band. More particularly, some example embodiments provide an architecture in which a host processor can be configured to define a coexistence policy for two or more radios that can be implemented on a wireless communication device. The coexistence policy of some example embodiments can define a priority between radios given a present use case context such that a radio can be given priority over another radio based on a given use case context. The host processor can provide the coexistence policy to the radios via an interface between the host processor and the radios.

The radios can be configured to exchange state information via a separate interface between the radios. The interface between the radios can be a higher speed interface, which can facilitate real time exchange of state information between the radios. The state information can, for example, be indicative of interference conditions experienced by a radio, operating state information indicative of whether a radio is transmitting or receiving data during a given time period, and/or the like. In this regard, state information that can change frequently (e.g., in real time) can be exchanged between radios via an interface that can facilitate relatively high speed communication between radios. In this regard, some example embodiments partition information that can be used by a radio to make a decision for controlling radio operation to mitigate in-device interference into non-real time information that does not change relatively frequently, such as coexistence policies, and state information for the co-located radio(s) that can change frequently over time. The coexistence policies and/or other non-real time information that may not change with a great deal of regularity can accordingly be communicated between a host processor and radios via a slower speed interface(s) and/or shared interface via which other information can be communicated without clogging a higher speed, direct interface between radios.

A radio in accordance with some example embodiments can use state information received from another radio to control radio operation in accordance with the coexistence policy provided by the host processor. In this regard, a radio can have knowledge of conditions experienced by and/or activities being performed by a co-located radio based on the state information and can use this knowledge to determine whether to modify radio operation to mitigate interference with the co-located radio in accordance with the coexistence policy at a given time.

This Summary is provided merely for purposes of summarizing some example embodiments so as to provide a basic understanding of some aspects of the disclosure. Accordingly, it will be appreciated that the above described example embodiments are merely examples and should not be construed to narrow the scope or spirit of the disclosure in any way. Other embodiments, aspects, and advantages will become apparent from the following detailed description taken in conjunction with the accompanying drawings which illustrate, by way of example, the principles of the described embodiments.

BRIEF DESCRIPTION OF THE DRAWINGS

The described embodiments and the advantages thereof may best be understood by reference to the following description taken in conjunction with the accompanying drawings. These drawings are not necessarily drawn to scale, and in no way limit any changes in form and detail that may be made to the described embodiments by one skilled in the art without departing from the spirit and scope of the described embodiments.

DETAILED DESCRIPTION OF SELECTED EMBODIMENTS

Some example embodiments address an in-device coexistence problem between radios using disparate wireless communication technologies. In this regard, wireless communication devices often include multiple radios, each of which can implement one or more disparate wireless communication technologies, which coexist on the device. For example, a cellular radio, such as a Long Term Evolution (LTE) radio, can coexist on a device along with one or more connectivity radios, such as a Bluetooth radio, WLAN (e.g., Wi-Fi) radio, and/or the like. In embodiments including a Wi-Fi Radio, the Wi-Fi radio can implement an Institute of Electrical and Electronics Engineers (IEEE) 802.11 technology, such as one or more of: IEEE 802.11a; IEEE 802.11b; IEEE 802.11g; IEEE 802.11-2007; IEEE 802.11n; IEEE 802.11-2012; IEEE 802.11ac; or other present or future developed IEEE 802.11 technologies. The connectivity radio can use an ISM band. For example, Bluetooth can operate in the 2.4 GHz ISM band, while a WLAN radio can operate in the 2.4 GHz and/or 5 GHz ISM bands. The cellular radio and/or connectivity radio(S) can further coexist with a Global Navigation Satellite System (GNSS) radio, such as a Global Positioning System (GPS) radio, GLONASS radio, and/or other GNSS radio, which can operate in the 1.6 GHz band.

Concurrent operation of multiple radios on a wireless communication device can result in interference between radios. In this regard, interference can result from a transmission emitted by a radio using an aggressor technology while a radio is receiving data via a victim technology. In such situations, the aggressor technology transmissions can inhibit data reception via the victim technology, potentially resulting in received data errors, or in extreme cases, even completely deafening the victim technology receiver. This radio frequency (RF) interference can be caused by a number of side effects that can result from concurrent radio operation on a device.

Figure 1:
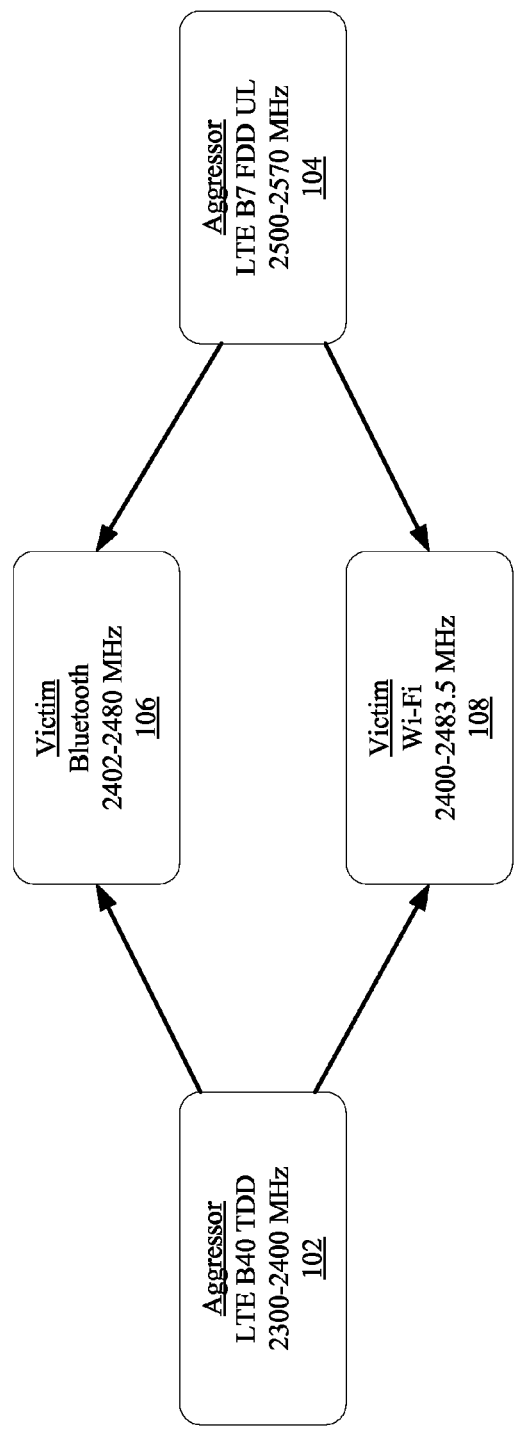
FIG. 1 illustrates an example of adjacent channel interference that can be addressed by some example embodiments.

For example, RF interference can result from adjacent channel interference (ACI), in which transmit energy spills over into adjacent bands. FIG. 1 illustrates an example of ACI that can be addressed by some example embodiments. In this regard, one or more cellular bands can be adjacent to an ISM band that can be used by a connectivity radio. In the example of FIG. 1, LTE band 40 using time-division duplexing (TDD) 102 can operate in the 2300-2400 MHz band range, while LTE band 7 using frequency-division duplexing (FDD) for uplink (UL) communications 104 can operate in the 2500-2570 MHz band range. The LTE bands 102 and 104 can act as aggressor bands such that transmissions via these bands can interfere with reception via connectivity radios operating in the adjacent 2400 GHz ISM band. For example, as illustrated in FIG. 1, a Bluetooth radio operating in the 2402-2480 MHz band 106 and a Wi-Fi radio operating in the 2400-2483.5 MHz band 108 can suffer as victims from adjacent channel interference resulting from the LTE bands 102 and 104, as transmit energy from LTE bands 102 and 104 can spill over into the bands 106 and 108 and can desense the Bluetooth and Wi-Fi radios, potentially interfering with data reception by the Bluetooth and Wi-Fi radios.

As another example, intermodulation distortion can result in RF interference that can harm reception by a radio. In this regard, harmonics can be generated when two or more transmit frequencies "mix" with each other due to non-linearity. For example, cellular bands 5 and/or 8 can mix with 2.4 GHz ISM band transmissions to desense a GNSS receive band. As still a further example, RF interference can result from harmonic distortion in which harmonics can be generated from a single transmit frequency due to a non-linearity.

For example, when a device communicates concurrently via cellular communications and a lower powered communication technology, such as an IEEE 802.15 wireless personal area network (PAN) communication technology (e.g., Bluetooth and/or other wireless PAN communication technology) or WLAN technology, which can, for example, utilize an ISM band, cellular transmissions can prevent data reception via the lower powered technology. Some example embodiments facilitate in-device coexistence between wireless communication technologies by mitigating such in-device interference conditions.

Several example embodiments described herein can facilitate in-device coexistence between radios by mitigating the effects of such RF interference conditions. In this regard, some example embodiments provide an architecture and corresponding methods, apparatuses, and computer program products for facilitating in-device coexistence between radios. More particularly, some example embodiments provide an architecture in which a host processor can be configured to define a coexistence policy for two or more radios (e.g., a cellular radio, a connectivity radio(s), a GNSS radio, and/or the like) that can be implemented on a wireless communication device. The coexistence policy of some example embodiments can define a priority between radios given a present use case context such that a radio can be given priority over another radio based on a given use case context. The host processor can provide the coexistence policy to the radios via an interface between the host processor and the radios.

The radios of such example embodiments can be configured to exchange state information via a separate interface between the radios. The interface between the radios can be a higher speed interface, which can facilitate real time exchange of state information between the radios. The state information can, for example, be indicative of interference conditions experienced by a radio, operating state information indicative of whether a radio is transmitting or receiving data during a given time period, and/or the like. As such, state information that can change frequently and/or which requires low-latency communication (e.g., in real time) can be exchanged between radios via an interface that can facilitate relatively high speed communication between radios. In this regard, some example embodiments partition information that can be used by a radio to make a decision for controlling radio operation to mitigate in-device interference into non-real time information that does not change relatively frequently, such as coexistence policies, and state information for the co-located radio(s) that can change frequently over time. The coexistence policies and/or other non-real time information that may not change frequently can accordingly be communicated between a host processor and radios via a slower speed interface(s) and/or shared interface via which other information can be communicated without clogging a higher speed, direct interface between radios.

A radio in accordance with some example embodiments can use state information received from another radio to control radio operation in accordance with the coexistence policy provided by the host processor. In this regard, a radio can have knowledge of conditions experienced by and/or activities being performed by a co-located radio based on the state information and can use this knowledge to determine whether to modify radio operation to mitigate interference with the co-located radio in accordance with the coexistence policy at a given time. Thus, for example, an aggressor radio, such as a cellular radio, can know from the state information whether a victim radio, such as a Bluetooth radio, is receiving data at a given time and, if the victim radio is receiving data at a given time and has a higher defined priority based on the coexistence policy, the aggressor radio can take action, such as backing off transmission power, to mitigate interference with data reception by the victim radio. If, however, the victim radio is not receiving data at a given time, the aggressor radio can know based on the state information that it can transmit data without regard for the victim radio at that point in time, even if the victim radio has a higher priority based on the coexistence policy.

Figure 2:
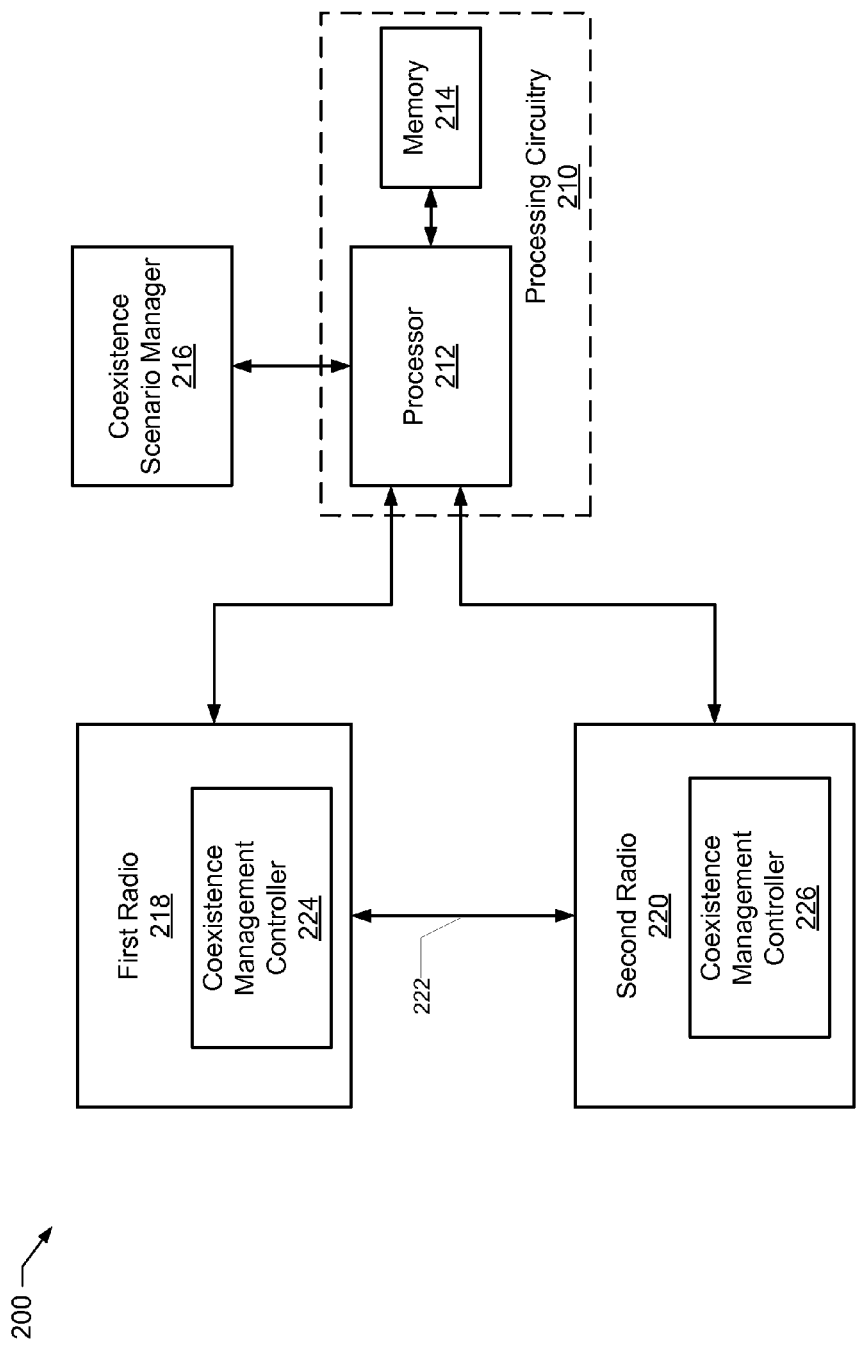
FIG. 2 illustrates a block diagram of a wireless communication device in accordance with some example embodiments.

Referring now to FIG. 2, FIG. 2 illustrates a block diagram of a wireless communication device 200 in accordance with some example embodiments. The wireless communication device 200 can be any device including two or more co-located radios, which can enable the device to communicate via multiple wireless communication technologies. By way of non-limiting example, the wireless communication device 200 can be a mobile phone, tablet computing device, laptop computer, or other computing device that can include multiple radios. It will be appreciated that the components, devices or elements illustrated in and described with respect to FIG. 2 below may not be mandatory and thus some may be omitted in certain embodiments. Additionally, some embodiments can include further or different components, devices or elements beyond those illustrated in and described with respect to FIG. 2.

In some example embodiments, the wireless communication device 200 can include processing circuitry 210 that is configurable to perform actions in accordance with one or more example embodiments disclosed herein. In this regard, the processing circuitry 210 can be configured to perform and/or control performance of one or more functionalities of the wireless communication device 200 in accordance with various example embodiments, and thus can provide means for performing functionalities of the wireless communication device 200 in accordance with various example embodiments. The processing circuitry 210 may be configured to perform data processing, application execution and/or other processing and management services according to one or more example embodiments. In some embodiments, the wireless communication device 200 or a portion(s) or component(s) thereof, such as the processing circuitry 210, can include one or more chips, or one or more chipsets. The processing circuitry 210 and/or one or more further components of the wireless communication device 200 can therefore, in some instances, be configured to implement an embodiment on a single chip or chipset.

In some example embodiments, the processing circuitry 210 can include a processor 212 and, in some embodiments, such as that illustrated in FIG. 2, can further include memory 214. The processing circuitry 210 can be in communication with or otherwise control a coexistence scenario manager 216 and two or more radios that can be implemented on the wireless communication device 200, including a first radio 218 and second radio 220.

The processor 212 can be embodied in a variety of forms. For example, the processor 212 can be embodied as various hardware-based processing means such as a microprocessor, a coprocessor, a controller or various other computing or processing devices including integrated circuits such as, for example, an ASIC (application specific integrated circuit), an FPGA (field programmable gate array), some combination thereof, or the like. The processor 212 of some example embodiments can be a host processor configured to serve as a host for controlling or otherwise facilitating operation of two or more device radios, such as the first radio 218 and second radio 220. In some example embodiments, the processor 212 can be an application processor. Although illustrated as a single processor, it will be appreciated that the processor 212 can comprise a plurality of processors. The plurality of processors can be in operative communication with each other and can be collectively configured to perform one or more functionalities of the wireless communication device 200 as described herein. In some example embodiments, the processor 212 can be configured to execute instructions that can be stored in the memory 214 or that can be otherwise accessible to the processor 212. As such, whether configured by hardware or by a combination of hardware and software, the processor 212 capable of performing operations according to various embodiments while configured accordingly.

In some example embodiments, the memory 214 can include one or more memory devices. Memory 214 can include fixed and/or removable memory devices. In some embodiments, the memory 214 can provide a non-transitory computer-readable storage medium that can store computer program instructions that can be executed by the processor 212. In this regard, the memory 214 can be configured to store information, data, applications, instructions and/or the like for enabling the wireless communication device 200 to carry out various functions in accordance with one or more example embodiments. In some embodiments, the memory 214 can be in communication with one or more of the processor 212, coexistence scenario manager 216, first radio 218, or second radio 220 via a bus(es) for passing information among components of the wireless communication device 200.

The wireless communication device 200 can further include coexistence scenario manager 216, which can be embodied as various means, such as circuitry, hardware, a computer program product comprising a computer readable medium (for example, the memory 214) storing computer readable program instructions executable by a processing device (for example, the processor 212), or some combination thereof. In some embodiments, the processor 212 (or the processing circuitry 210) can include, or otherwise control the coexistence scenario manager 216. As will be described further herein below, the coexistence scenario manager 216 can be configured to define a coexistence policy for two or more radios on the wireless communication device 200, such as the first radio 218 and second radio 220, and can provide the coexistence policy to the radios for implementation.

As noted, the wireless communication device 200 can include a plurality of co-located radios. Two such radios—the first radio 218 and second radio 220—are illustrated by way of example in FIG. 2. It will be appreciated, however, that the wireless communication device 200 can include one or more further radios in some example embodiments. The radios implemented on the wireless communication device 200 can each implement any respective wireless communication technology such that two or more disparate wireless communication technologies can be implemented on the wireless communication device 200. For example, in some example embodiments, one or more radios on the wireless communication device 200, such as one or more of the first radio 218 or second radio 220, can implement a cellular communication technology, such as a Long Term Evolution (LTE) cellular communication technology, a Universal Mobile Telecommunications System (UMTS) cellular communication technology, a Global System for Mobile Communications (GSM) cellular communication technology, a Code Division Multiple Access (CDMA) cellular communication technology, or a CDMA 2000 cellular communication technology, and/or the like. As a further example, in some example embodiments, one or more radios on the wireless communication device 200, such as one or more of the first radio 218 or second radio 220, can be a connectivity radio implementing a communications technology, such as Bluetooth, Zigbee, and/or other wireless personal area network (PAN) technology; and/or Wi-Fi and/or other wireless local area network (WLAN) communication technology. In some example embodiments, in which one or more of the first radio 218 or second radio 220 is a connectivity radio, the connectivity radio can implement a wireless communication technology using an ISM band. As still a further example, the wireless communication device 200 of some example embodiments can include a GNSS radio. It will be appreciated, however, that the foregoing example radio technologies are provided by way of example, and not by way of limitation, as various example embodiments support in-device coexistence between any two (or more) radios that use disparate wireless communication technologies.

An interface 222 can be used to interface two or more radios, such as the first radio 218 and second radio 220, on the wireless communication device 200. The interface 222 can be separate from an interface(s) between the processor 212 and the first radio 218 and second radio 220. The interface 222 can be a higher speed interface than the interface(s) between the radios and processor 212, which can offer low latency to allow (e.g., on the order of microseconds) for communication of real time state information between radios. The interface 222 of some example embodiments can be an interface dedicated to the exchange of information between radios, which may not be used for communication of information to or from non-radio components of the wireless communication device 200. In some example embodiments, the interface 222 can be a direct interface linking the first radio 218 and second radio 220 (and potentially one or more further radios). In some example embodiments, the interface 222 can be a Wireless Coexistence Interface (WCI), such as a WCI-2 interface, WCI-1 interface, or other type of WCI. It will be appreciated, however, that WCI interface types are but one example of an interface that can be used to facilitate communication of state information between radios, and any appropriate interface that can be used to interface two or more radios to support the exchange of state information between radios can be used in addition to or in lieu of an WCI interface in accordance with some example embodiments.

In some example embodiments, radios implemented on the wireless communication device 200 can include respective coexistence management controllers. For example, a first radio coexistence management controller 224 can be implemented on the first radio 218 and a second radio coexistence management controller 226 can be implemented on the second radio 220. The coexistence management controllers (e.g., the first radio coexistence management controller 224 and the second radio coexistence management controller 226) can be embodied as various means, such as circuitry, hardware, a computer program product comprising computer readable program instructions stored on a computer readable medium that can be implemented on a radio and executed by a processing device that can be implemented on a radio, or some combination thereof.

The coexistence scenario manager 216 can be configured to define a coexistence policy for radios implemented on the wireless communication device 200, such as the first radio 218 and second radio 220. The coexistence policy can, for example define priority levels across device radios, such as cellular, GNSS, Bluetooth, Wi-Fi, and/or the like. In this regard, the coexistence scenario manager 216 can maintain a "global" view of the priority levels across the various radios. The coexistence policy can be defined based on a present use case context of the wireless communication device 200. For example, a different coexistence policy can be defined and implemented in a use case context in which a user of a cellular phone is using a Bluetooth headset while on an active cellular call than in a use case context in which a user is engaged in an active data session over a cellular connection. As such, use case context-based coexistence priority levels in accordance with some example embodiments can change relatively slowly in non-real time over time in response to event triggers.

The coexistence scenario manager 216 can be further configured to push the coexistence policy down to the device radios via an interface(s) between the processor 212 and the device radios. The interface(s) between the processor 212 and the first radio 218 and second radio 220 can be a non-real time interface(s). Communication of the coexistence policy to the radios can be primarily event-triggered. In this regard, the coexistence policy can be changed in response to event triggers as the use case context of the device changes over time, such as in response to user activity.

Implementation and execution of the coexistence policy can be performed by the coexistence management controllers on the radios based on coordination amongst the radios via the interface 222. In this regard, the coexistence management controllers (e.g., the first radio coexistence management controller 224 and the second radio coexistence management controller 226) can be configured to perform measurements and exchange state information between the radios via the interface 222. As will be described further herein below, the state information can include an indication of an interference condition experienced by a radio, operating state information for a radio, and/or other information that can be used by a coexistence management controller to determine whether to modify radio operation to mitigate interference with another radio in accordance with the coexistence policy at a given time.

A coexistence management controller, such as the first radio coexistence management controller 224 and the second radio coexistence management controller 226, on a radio can perform real-time actions to control radio operation based on a coexistence policy defined by the coexistence scenario manager 216 and one or more of state information that can be provided by a co-located radio or measurements that can be made by the radio. In this regard, a coexistence management controller can determine whether to take corrective action to mitigate interference with a co-located radio in accordance with a coexistence policy based on measurements that can be made by the radio and/or state information that can be provided by the co-located radio.

As such, it will be appreciated that some example embodiments partition information that can be used by a coexistence management controller, such as the first radio coexistence management controller 224 and the second radio coexistence management controller 226, to make a decision for controlling radio operation to mitigate in-device interference into non-real time information that does not change relatively frequently, such as coexistence policies, and real time state information for the co-located radio(s) that can change frequently over time. The coexistence policies and/or other non-real time information that may not change with a great deal of regularity can accordingly be communicated to the first radio 218 and second radio 220 by the processor 212 via a slower speed interface(s) and/or shared interface (e.g., a shared bus) via which other information can be communicated between device components. Real time state information for the radios can be communicated via the interface 222, which can offer lower latency for communication of state information that can change relatively frequently (e.g., in real time) between the radios to allow for coordination between radios. As non-real time information can be provided to the radios via another interface(s), the interface 222 provision of the non-real time information to the device radios does not clog the interface 222 or otherwise cause a delay in communication of real time state information between radios.

A coexistence management controller implemented on a radio, such as the first radio coexistence management controller 224 and the second radio coexistence management controller 226, can use any appropriate technique to control radio operation to take corrective action so as to mitigate interference with a co-located radio when determined to be appropriate in accordance with a coexistence policy. In this regard, a coexistence management controller can use one or more hardware-based techniques and/or one or more software-based techniques for reducing interference.

As an example of a hardware-based technique that can be used, a coexistence management controller in accordance with some example embodiments can be configured to modify filtering that can be applied to transmissions, such as by applying sharper filtering to aggressor radio transmissions to reduce adjacent channel interference with a victim radio. As another example hardware-based technique that can be used by a coexistence management controller to mitigate interference, a coexistence management controller in accordance with some example embodiments can be configured to adjust a linearity of RF components of an aggressor radio, such as by reducing or increasing linearity as appropriate, to mitigate the effects of intermodulation distortion and/or harmonic distortion interference with a victim radio.

As an example of a software-based technique that can be used, a coexistence management controller in accordance with some example embodiments can be configured to apply time domain sharing techniques to mitigate the effects of interference. In this regard, if a victim radio has lower priority than an aggressor radio, the coexistence management controller on the victim radio can avoid receiving data when an aggressor radio(s) is (are) transmitting. The coexistence management controller on the victim radio can know whether the aggressor radio is transmitting at a given time based on state information that can be provided by the aggressor radio (e.g., via interface 222) and/or based on measurements that can be performed by the victim radio. Similarly, if a victim radio is defined by the coexistence policy to have higher priority than an aggressor radio during a particular time period and is receiving data during the time period, the coexistence management controller on the aggressor radio can avoid transmitting data during the victim radio's high priority reception period. The coexistence management controller on the aggressor radio can know whether the victim radio is receiving data during a time period based on state information that can be provided by the victim radio (e.g., via interface 222) and/or based on measurements that can be performed by the aggressor radio.

As another example of a software-based technique that can be used, a coexistence management controller in accordance with some example embodiments can be configured to apply frequency domain exclusion techniques to mitigate interference with a co-located radio. For example, a coexistence management controller on a victim radio can be configured to avoid reception on a frequency channel(s) affected by aggressor radio transmissions, if avoiding reception on the affected channel(s) is possible. The coexistence management controller on the victim radio can, for example, have knowledge of a frequency channel affected by aggressor radio transmissions based on measurements that can be performed by the victim radio. The channel(s) affected by the aggressor transmissions can, for example, be the channel(s) within a band used by the victim radio immediately adjacent to a band used by the aggressor radio. In some example embodiments, the coexistence management controller on the victim radio can be configured to apply frequency domain exclusion techniques during periods which the aggressor radio is known by the victim radio to be transmitting. In this regard, the coexistence management controller on the victim radio can know whether the aggressor radio is transmitting at a given time based on state information that can be provided by the aggressor radio (e.g., via interface 222) and/or based on measurements that can be performed by the victim radio.

A coexistence management controller on an aggressor radio can, for example, be configured to apply frequency domain exclusion techniques to avoid transmission on a channel(s) that can be more damaging to a victim radio, if avoiding transmission on the channel(s) is possible. The channel(s) that can be more damaging to the victim radio can, for example, be the channel(s) within a band used by the aggressor radio immediately adjacent to a band used by the victim radio. In some example embodiments, the coexistence management controller on the aggressor radio can be configured to apply frequency domain exclusion techniques during periods which the victim radio is known by the aggressor radio to be receiving data. In this regard, the coexistence management controller on the aggressor radio can know whether the victim radio is receiving at a given time based on state information that can be provided by the victim radio (e.g., via interface 222) and/or based on measurements that can be performed by the aggressor radio.

As a further example of a software-based technique that can be used, a coexistence management controller in accordance with some example embodiments can be configured to apply power domain exclusion techniques to mitigate interference with a co-located radio. For example, if there are multiple aggressor radios on a device, a coexistence management controller on a first aggressor radio can avoid transmitting concurrently with the second aggressor radio so as to limit the total transmission power emitted by the device and/ or to avoid causing intermodulation distortion to mitigate interference with a victim radio. In this example, the coexistence policy may accord a lower priority to the first aggressor radio than to the second aggressor radio and the victim radio such that the coexistence management controller on the first aggressor radio can back off and avoid transmitting, thereby yielding to transmission by the first aggressor radio and mitigating interference with the victim reference. The coexistence management controller on the first aggressor radio can determine to avoid transmitting based on knowledge of whether the second aggressor radio is transmitting at a given time and/or whether the victim radio is receiving at a given time. In this regard, the coexistence management controller on the first aggressor radio can know whether the second aggressor radio is transmitting and/or whether the victim radio is receiving during a given period of time based on state information that can be provided by the second aggressor radio and/or by the victim radio (e.g., via interface 222) and/or based on measurements that can be performed by the first aggressor radio.

As another example of a power domain exclusion technique that can be implemented by the coexistence management controller of an aggressor radio is backing off transmission power of the aggressor radio if the victim radio is receiving. In this regard, limiting the transmission power can reduce a level of interference with reception by the victim radio. The coexistence management controller can know whether the victim radio is receiving during a given period of time based on state information that can be provided by the victim radio (e.g., via interface 222) and/or based on measurements that can be performed by the aggressor radio.

Figure 3:
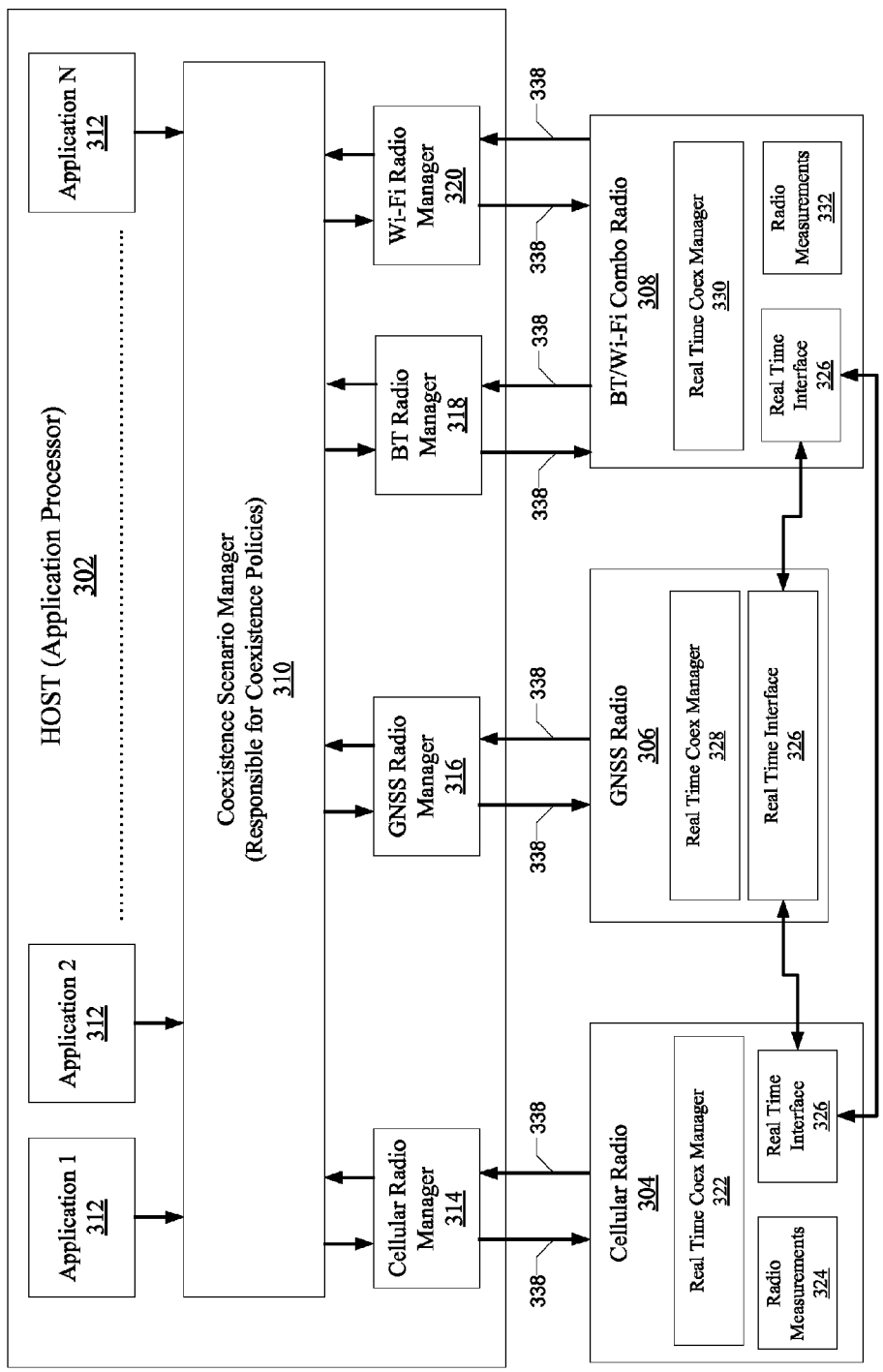
FIG. 3 illustrates an architecture for facilitating in-device coexistence between radios in accordance with some example embodiments.

FIG. 3 illustrates an example architecture for facilitating in-device coexistence between radios in accordance with some example embodiments. The architecture can include a HOST 302, which can be embodied as an application processor. The HOST 302 can, for example, be an embodiment of the processor 212 and/or of the processing circuitry 210. The architecture can further include a plurality of radios. In the example of FIG. 3, the architecture can include a cellular radio 304, a GNSS radio 306, and a Bluetooth (BT)/Wi-Fi combo radio 308. It will be appreciated, however, that the combination of radios illustrated in FIG. 3 is illustrated by way of example, and not by way of limitation. In this regard, one or more of the cellular radio 304, GNSS radio 306, and BT/Wi-Fi combo radio 308 can be omitted in some example embodiments. Further, in some example embodiments, the architecture can include one or more other radios in addition to or in lieu of the radios illustrated in and described with respect to FIG. 3. Moreover, the use of a BT/Wi-Fi combo radio is by way of example, and some example embodiments can include a standalone Bluetooth radio and/or a standalone Wi-Fi radio. As such, it will be appreciated that the architectural structure and corresponding techniques illustrated in and described with respect to FIG. 3 can be applied mutatis mutandis to any combination of radios that can be implemented on a wireless communication device.

The HOST 302 can include a coexistence scenario manager 310, which can be responsible for defining coexistence policies for the device radios and providing the coexistence policies to the device radios. In this regard, the coexistence scenario manager 310 can, for example, be an embodiment of the coexistence scenario manager 216. One or more applications 312 can be running on the HOST 302. The coexistence scenario manager 310 can accordingly have knowledge of the application(s) 312 that are active at a given time. In some example embodiments, the coexistence scenario manger 310 can determine corresponding use case state information for active applications. In this regard, the coexistence scenario manager 310 can leverage knowledge of a state of applications 312 to derive a global view of the device usage and determine a present use case context for the device. The coexistence scenario manager 310 can be configured to define a coexistence policy for the device radios based at least in part on the present use case context. The coexistence policy can include a definition of one or more priorities between device radios with respect to the use case context.

The coexistence scenario manager 310 can be configured to provide a defined coexistence policy to the device radios via respective radio manager intermediaries that can be implemented on the HOST 302. For example, a cellular radio manager 314 can facilitate communication between the coexistence scenario manager 310 and cellular radio 304. A GNSS radio manager 316 can facilitate communication between the coexistence scenario manager 310 and GNSS radio 306. A BT radio manager 318 can facilitate communication between the coexistence scenario manager 310 and the BT portion of the BT/Wi-Fi combo radio 308. A Wi-Fi radio manager 320 can facilitate communication between the coexistence scenario manager 310 and the Wi-Fi portion of the BT/Wi-Fi combo radio 308.

The coexistence scenario manager 310 can be configured to use an interface(s) 338 to provide a coexistence policy to the radios (e.g., via the respective radio manager intermediaries 314-320). The interface(s) 338 can be a non-real time interface(s), which can be used for large message transfers, and which may have a delay on the order of milliseconds. The interface(s) 338 of some example embodiments can be shared by components of a wireless communication device in addition to the HOST 302 and radios 304-308, and can be used for the communication of data in addition to coexistence policies and/or other information that can be exchanged between the HOST 302 and the radios 304-308.

The cellular radio 304 can include a real time coex manager 322, which can be configured to implement and execute a coexistence policy defined by the coexistence scenario manager 310. In this regard, the real time coex manager 322 can, for example, be an embodiment of a coexistence management controller (e.g., the coexistence management controller 224 or coexistence management controller 226) described with respect to FIG. 2. The real time coex manager 322 can be configured to use radio measurements 324 that can be made by the cellular radio 304 and/or state information received from the GNSS radio 306 and/or from the BT/Wi-Fi combo radio 308 via the real time interface 326 to make control decisions for controlling the cellular radio 304 in accordance with the coexistence policy so as to mitigate interference with the GNSS radio 306 and/or with the BT/Wi-Fi Combo radio 308.

The real time interface 326 can be an interface offering a low latency, such as a delay on the order of microseconds, to allow for communication of real time state information between radios to facilitate coordination between radios in accordance with a coexistence policy defined and handed down by the coexistence scenario manager 310. In some example embodiments, the real time interface 326 can be a WCI interface, such as a WCI-2 interface or WCI-1 interface. The real time interface 326 of some example embodiments can be an interface dedicated to the exchange of information between radios, which may not be used for communication of information to or from non-radio components.

The real time coex manager 322 can be further configured to provide state information for the cellular radio 304 to the GNSS radio 306 and/or to the BT/Wi-Fi combo radio 308 via the real time interface 326. The state information can include any information about a state of the cellular radio 304 that can be used by the GNSS radio 306 and/or by the BT/Wi-Fi combo radio 308 to make determinations for radio operation control in compliance with a coexistence policy defined by the coexistence scenario manager 310. For example, the state information can include operating state information indicative of whether the cellular radio 304 is receiving or transmitting data during one or more time periods. The state information can additionally or alternatively include an indication of an interference condition that may be experienced by the cellular radio 304, such as can be determined by the cellular radio 304 based on the radio measurements 324.

The GNSS radio 306 can include a real time coex manager 328, which can be configured to implement and execute a coexistence policy defined by the coexistence scenario manager 310. In this regard, the real time coex manager 328 can, for example, be an embodiment of a coexistence management controller (e.g., the coexistence management controller 224 or coexistence management controller 226) described with respect to FIG. 2. The real time coex manager 328 can, for example, be configured to use measurements that can be made by the GNSSS radio 306 and/or state information received from the cellular radio 304 and/or from the BT/Wi-Fi combo radio 308 via the real time interface 326 to make control decisions for controlling the GNSS radio 306 in accordance with the coexistence policy so as to mitigate interference with the cellular radio 304 and/or with the BT/Wi-Fi Combo radio 308.

The real time coex manager 328 can be further configured to provide state information for the GNSS radio 306 to the cellular radio 304 and/or to the BT/Wi-Fi combo radio 308 via the real time interface 326. The state information can include any information about a state of the GNSS radio 306 that can be used by the cellular radio 304 and/or by the BT/Wi-Fi combo radio 308 to make determinations for radio operation control in compliance with a coexistence policy defined by the coexistence scenario manager 310. For example, the state information can include operating state information indicative of whether the GNSS radio 306 is receiving or transmitting data during one or more time periods. The state information can additionally or alternatively include an indication of an interference condition that may be experienced by the GNSS radio 306, such as can be determined based on measurements that can be made by the GNSS radio 306.

The BT/Wi-Fi combo radio 308 can include a real time coex manager 330, which can be configured to implement and execute a coexistence policy defined by the coexistence scenario manager 310. In this regard, the real time coex manager 330 can, for example, be an embodiment of a coexistence management controller (e.g., the coexistence management controller 224 or coexistence management controller 226) described with respect to FIG. 2. The real time coex manager 330 can be configured to use radio measurements 332 that can be made by the BT/Wi-Fi combo radio 308 and/or state information received from the cellular radio 304 and/or from the GNSS radio 306 via the real time interface 326 to make control decisions for controlling the BT/Wi-Fi combo radio 308 in accordance with the coexistence policy so as to mitigate interference with the cellular radio 304 and/or with the GNSS radio 306.

The real time coex manager 330 can be further configured to provide state information for the BT/Wi-Fi combo radio 308 to the cellular radio 304 and/or to the GNSS radio 306 via the real time interface 326. The state information can include any information about a state of the BT/Wi-Fi combo radio 308 that can be used by the cellular radio 304 and/or by the GNSS radio 306 to make determinations for radio operation control in compliance with a coexistence policy defined by the coexistence scenario manager 310. For example, the state information can include operating state information indicative of whether the BT/Wi-Fi combo radio 308 is receiving or transmitting data during one or more time periods. The state information can additionally or alternatively include an indication of an interference condition that may be experienced by the BT/Wi-Fi combo radio 308, such as can be determined by the BT/Wi-Fi combo radio 308 based on the radio measurements 332.

Figure 4:
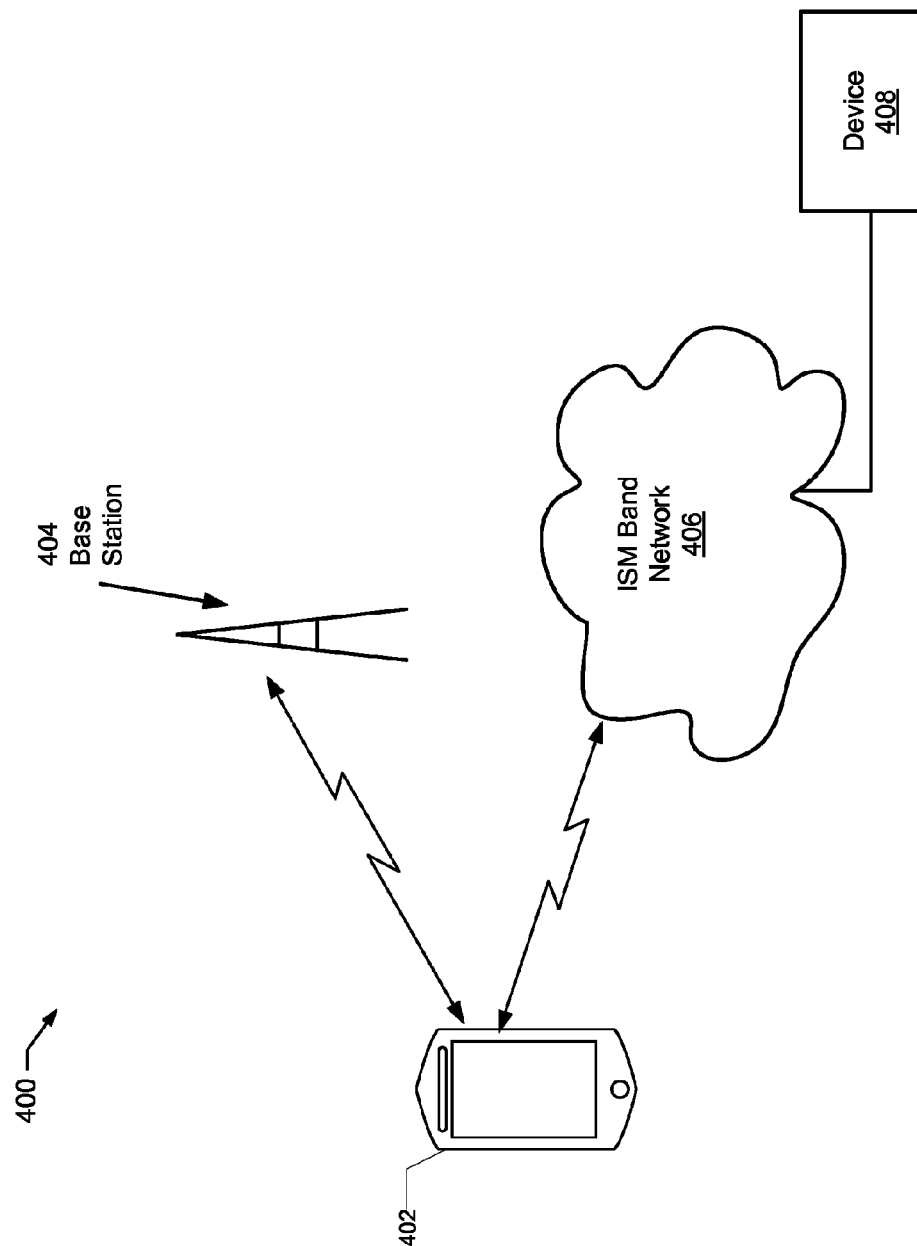
FIG. 4 illustrates an example system in which some example embodiments can be implemented to facilitate in-device coexistence between radios.

FIG. 4 illustrates an example system 400 in which some example embodiments can be implemented to facilitate in-device coexistence between wireless communication technologies. The system 400 can include a wireless communication device 402, which can, for example, be an embodiment of wireless communication device 200. The wireless communication device 402 can be configured to engage in cellular communications, which can be supported by a base station 402. For example, the wireless communication device 402 can be configured to engage in communication via a Long Term Evolution (LTE) cellular communication technology, a Universal Mobile Telecommunications System (UMTS) cellular communication technology, a Global System for Mobile Communications (GSM) cellular communication technology, a Code Division Multiple Access (CDMA) cellular communication technology, or a CDMA 2000 cellular communication technology, and/or other cellular communication technology. The wireless communication device 402 can be further configured to engage in communications via an ISM band technology. Thus, for example, the wireless communication device 402 can engage in wireless communications with a device 408 via an ISM band network 406. For example, in embodiments in which the ISM band network 406 is a Bluetooth network, the device 408 can be a Bluetooth headset or other Bluetooth device that can be interfaced with a wireless communication device.

In context of the system 400, various embodiments, can be implemented on the wireless communication device 402 to control operation of a cellular radio and/or ISM band radio(s) on the wireless communication device 402 to mitigate interference between the device radios in accordance with a coexistence policy to facilitate in-device coexistence between cellular and ISM band radios. It will be appreciated, however, that system 400 is provided merely by way of example. In this regard, as previously noted, some example embodiments facilitate in-device radio coexistence scenarios other than cellular and ISM band radio coexistence.

Figure 5:
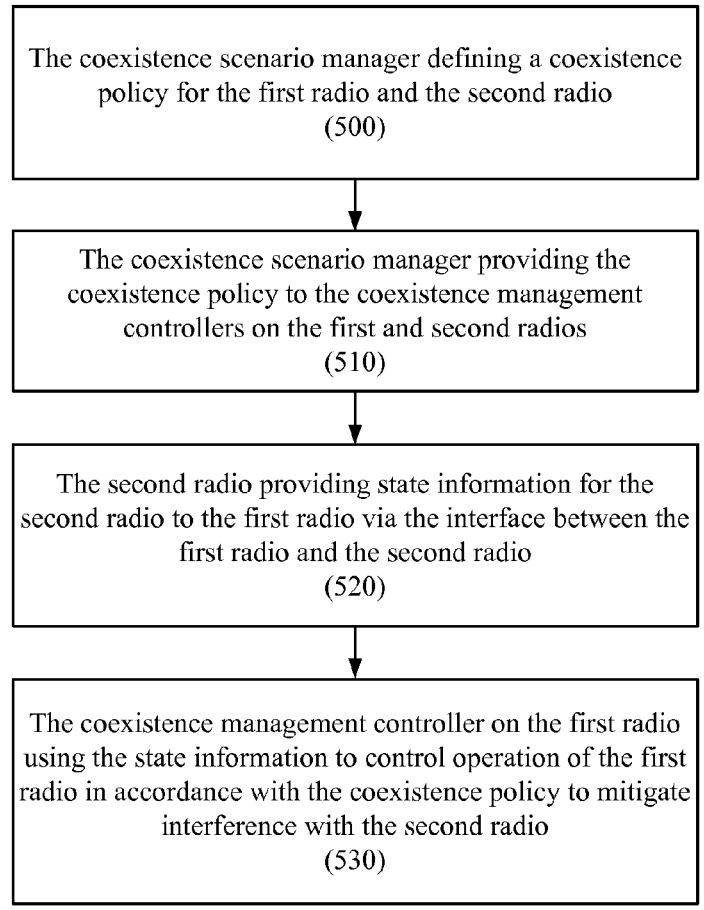
FIG. 5 illustrates a flowchart according to an example method that can be performed by a wireless communication device for facilitating in-device coexistence between radios according to some example embodiments.

FIG. 5 illustrates a flowchart according to an example method that can be performed by a wireless communication device for facilitating in-device coexistence between radios according to some example embodiments. In this regard, FIG. 5 illustrates operations that can be performed by the wireless communication device 200 and/or by the architecture illustrated in FIG. 3. The operations illustrated in and described with respect to FIG. 5 can, for example, be performed to facilitate in-device radio coexistence between cellular and ISM band radios, such as within the context of the system 400.

Operation 500 can include the coexistence scenario manager 216 defining a coexistence policy for the first radio 218 and the second radio 220. The coexistence policy can, for example, define a priority between the first radio 218 and the second radio 220. In some example embodiments, the coexistence policy can be defined based at least in part on a use case context of the wireless communication device, such that a different coexistence policy can be defined for a first use case context than for a second use case context.

Operation 510 can include the coexistence scenario manager 216 providing the coexistence policy to the first radio coexistence management controller 224 and the second radio management controller 226. The coexistence policy can be provided to the first radio 218 and second radio 220 via an interface(s) between the processor 210 and the radios.

The first radio 218 and/or the second radio 220 can exchange state information via the interface 222 to facilitate implementation of the coexistence policy by the first radio coexistence management controller 224 and second radio coexistence management controller 226. Thus, for example, operation 520 can include the second radio 220 providing state information for the second radio 220 to the first radio 218 via the interface 222. The state information can, for example, include an indication of an interference condition that may be experienced by the second radio 220. The state information can additionally or alternatively include operating state information indicating whether the second radio 220 is receiving or transmitting data during one or more time periods. It will be appreciated that the method can include the first radio 218 providing such state information to the second radio 220 in addition to or in lieu of operation 520.

Operation 530 can include the first radio coexistence management controller 224 using the state information received in operation 520 to control operation of the first radio 218 in accordance with the coexistence policy to mitigate interference with the second radio 220. Operation 530 can additionally or alternatively include the first radio coexistence management controller 224 using measurements that can be made by the first radio 218 to control operation of the first radio 218. For example, if the first radio 218 is an aggressor radio, such as a cellular radio, and the second radio 220 is a victim radio, such as a radio implementing an ISM band wireless communication technology, and the coexistence policy defines that the second radio 220 has priority over the first radio 218 in a given scenario, the first radio coexistence management controller 224 can control data transmission by the first radio 218 to mitigate interference with data reception by the second radio 220. In this regard, the first radio coexistence management controller 224 can use any hardware-based and/or software-based technique for mitigating interference, such as adjusting filtering of transmissions, adjusting linearity of RF components, time domain sharing techniques, frequency domain exclusion techniques, power domain techniques, some combination thereof, or the like to mitigate interference with reception by the second radio 220. It will be appreciated, however, that other scenarios are contemplated within the scope of the disclosure, including the first radio 218 being a victim radio, the second radio 220 being an aggressor radio, the first radio 218 using a wireless communication technology other than cellular, the second radio 220 using a non-ISM band wireless communication technology, the first radio 218 having priority over the second radio 220, coordination with one or more further co-located radios, or some combination thereof.

It will be appreciated that the method can include the second radio coexistence management controller 226 controlling operation of the second radio 220 in accordance with the coexistence policy in addition to or in lieu of operation 530. In this regard, the second radio coexistence management controller 226 can use state information for the first radio 218 that can be received via the interface 222 and/or measurements that can be made by the second radio 220 to control operation of the second radio 220 in accordance with the coexistence policy.

Figure 6:
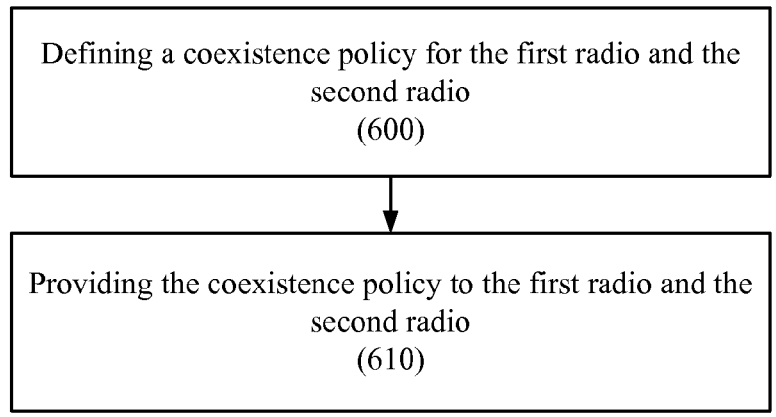
FIG. 6 illustrates a flowchart according to an example method that can be performed by a processor of a wireless communication device for facilitating in-device coexistence between radios according to some example embodiments.

FIG. 6 illustrates a flowchart according to an example method that can be performed by a processor of a wireless communication device for facilitating in-device coexistence between radios according to some example embodiments. In this regard, FIG. 6 illustrates operations that can, for example, be performed by processing circuitry 210, processor 212, coexistence scenario manager 216, HOST 302, coexistence scenario manager 310, some combination thereof, or the like.

Operation 600 can include the processor defining a coexistence policy for the first radio 218 and the second radio 220. The coexistence policy can, for example, define one or more priorities between radios. It will be appreciated that in devices having three or more radios, operation 600 can include defining a coexistence policy including the additional radios. Operation 610 can include the processor providing the coexistence policy to the first radio 218 and the second radio 220 via an interface(s) between the processor and the radios. The coexistence policy can configure coexistence management controllers on the radios (e.g., first radio coexistence management controller 224, second radio coexistence management controller 226, real time coex manager 322, real time coex manager 328, real time coex manager 330, and/or the like) to control operation of the radios based at least in part on state information that can be exchanged between the radios.

Figure 7:
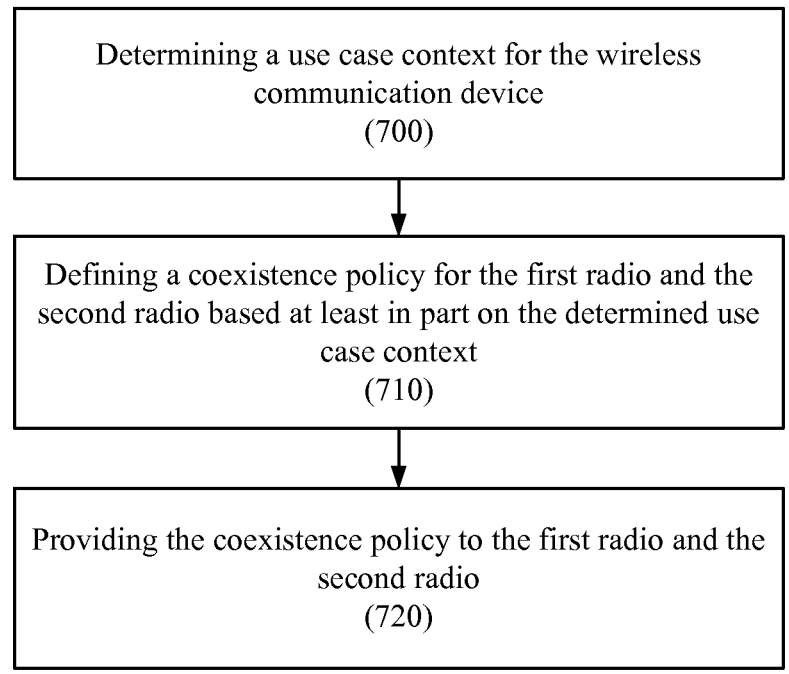
FIG. 7 illustrates a flowchart according to another example method that can be performed by a processor of a wireless communication device for facilitating in-device coexistence between radios according to some example embodiments.

FIG. 7 illustrates a flowchart according to another example method that can be performed by a processor of a wireless communication device for facilitating in-device coexistence between radios according to some example embodiments. In this regard, FIG. 7 illustrates an example method in which a coexistence policy can be defined based at least in part on a current use case context of a wireless communication device. Processing circuitry 210, processor 212, coexistence scenario manager 216, HOST 302, coexistence scenario manager 310, some combination thereof, or the like can, for example, provide means for performing the operations illustrated in and described with respect to FIG. 7.

Operation 700 can include the processor determining a use case context for the wireless communication device. The use case context can, for example, be determined based at least in part on a set of applications (e.g., applications 312) active on the device and/or a usage state of one or more such active applications. Operation 710 can include the processor defining a coexistence policy for the first radio 218 and the second radio 220 based at least in part on the determined use case context. The coexistence policy can, for example, define one or more priorities between radios. Thus, for example, one radio may have priority given a first use case context and another radio may have priority given a second use case context. It will be appreciated that in devices having three or more radios, operation 710 can include defining a coexistence policy including the additional radios. Operation 720 can include the processor providing the coexistence policy to the first radio 218 and the second radio 220 via an interface(s) between the processor and the radios. In this regard, operation 720 can correspond to operation 610 as described above. As use case context of the device changes over time, the method can return to operation 700, and the method can be repeated such that a new coexistence policy can be defined in response to a change in use case context.

Figure 8:
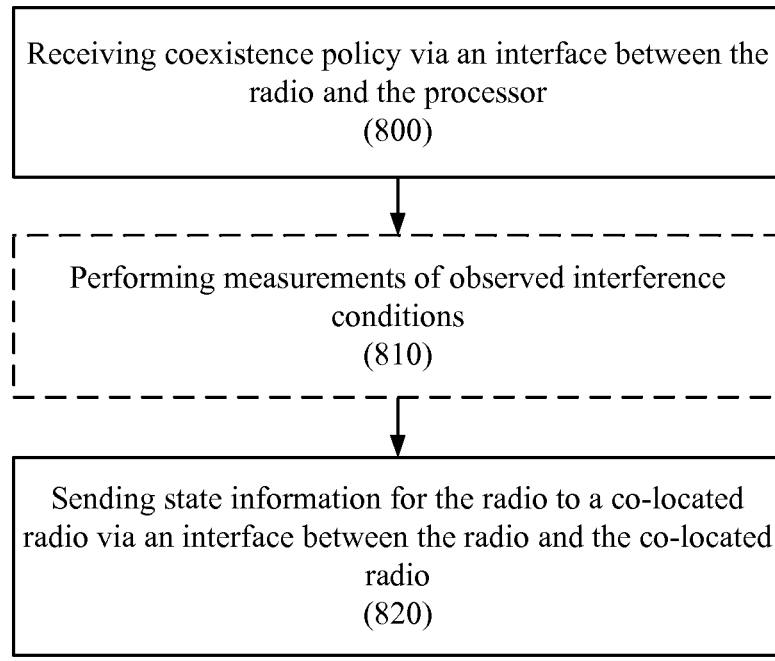
FIG. 8 illustrates a flowchart according to an example method that can be performed by a radio for facilitating in-device coexistence between radios according to some example embodiments.

FIG. 8 illustrates a flowchart according to an example method that can be performed by a radio for facilitating in-device coexistence between radios according to some example embodiments. In this regard, FIG. 8 illustrates a method that can be performed by the first radio 218, second radio 220, cellular radio 304, GNSS radio 306, BT/Wi-Fi combo radio 308, and/or other radio that can be implemented on a wireless communication device. A coexistence management controller (e.g., first radio coexistence management controller 224, second radio coexistence management controller 226, real time coex manager 322, real time coex manager 328, real time coex manager 330, and/or the like) can, for example, provide means for performing one or more of the operations illustrated in and described with respect to FIG. 8.

Operation 800 can include a radio receiving a coexistence policy via an interface between the radio and a host processor, such as the processor 212, HOST 302, or the like. The method can optionally further include operation 810, which can include the radio performing measurements. The measurements can, for example, include performing measurements of observed interference conditions, such as any observed errors in data reception, leakage from adjacent bands, harmonics, and/or other signals or frequencies that may result from operation of a co-located radio(s) and that may interfere with operation of the radio. Operation 820 can include the radio sending state information for the radio to a co-located radio(s) via an interface, such as interface 222 or interface 326, between the radio and the co-located radio(s). The state information can, for example, include operating state information indicative of whether the radio is receiving or transmitting data during one or more time periods. In embodiments including operation 810, the state information can additionally or alternatively include an indication of an interference condition experienced by the radio, as can be defined based on measurements that can be made by the radio.

Figure 9:
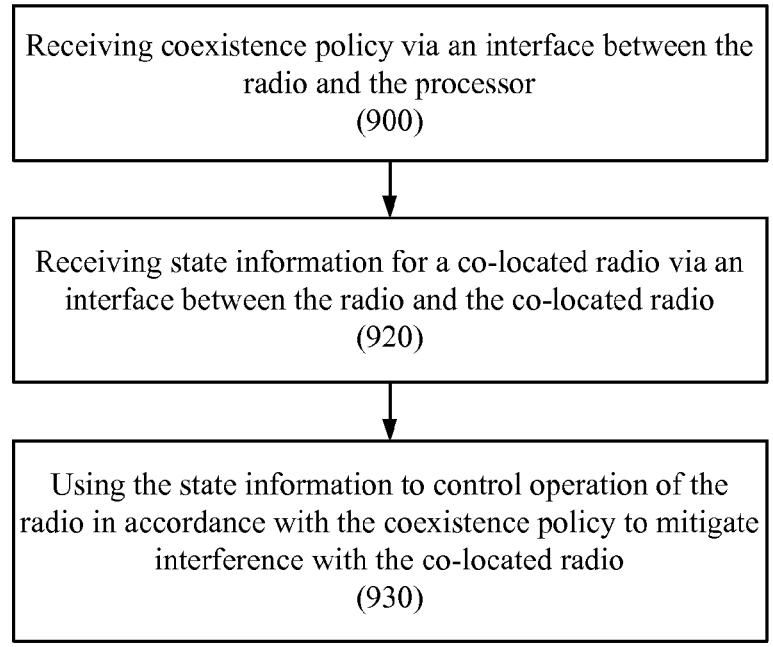
FIG. 9 illustrates a flowchart according to another example method that can be performed by a radio for facilitating in-device coexistence between radios according to some example embodiments.

FIG. 9 illustrates a flowchart according to another example method that can be performed by a radio for facilitating in-device coexistence between radios according to some example embodiments. In this regard, FIG. 9 illustrates a method that can be performed by the first radio 218, second radio 220, cellular radio 304, GNSS radio 306, BT/Wi-Fi combo radio 308, and/or other radio that can be implemented on a wireless communication device. A coexistence management controller (e.g., first radio coexistence management controller 224, second radio coexistence management controller 226, real time coex manager 322, real time coex manager 328, real time coex manager 330, and/or the like) can, for example, provide means for performing one or more of the operations illustrated in and described with respect to FIG. 9.

Operation 900 can include the radio receiving a coexistence policy via an interface between the radio and a host processor, such as the processor 212, HOST 302, or the like. Operation 920 can include the radio receiving state information for a co-located radio via an interface, such as interface 222 or interface 326, between the radio and the co-located radio. Thus, for example, operation 920 can include the radio receiving state information that can be provided by the co-located radio in accordance with performance of operation 820 by the co-located radio.

Operation 930 can include the radio using the state information for the co-located radio to control operation of the radio in accordance with the coexistence policy to mitigate interference with the co-located radio. It will be appreciated that the radio can use any hardware-based and/or software-based technique for mitigating interference, such as adjusting filtering of transmissions, adjusting linearity of RF components, time domain sharing techniques, frequency domain exclusion techniques, power domain techniques, some combination thereof, or the like to mitigate interference with the co-located radio.

The various aspects, embodiments, implementations or features of the described embodiments can be used separately or in any combination. Various aspects of the described embodiments can be implemented by software, hardware or a combination of hardware and software. The described embodiments can also be embodied as computer readable code on a computer readable medium for controlling manufacturing operations or as computer readable code on a computer readable medium for controlling a manufacturing line. The computer readable medium is any data storage device that can store data which can thereafter be read by a computer system. Examples of the computer readable medium include read-only memory, random-access memory, CD-ROMs, HDDs, DVDs, magnetic tape, and optical data storage devices. The computer readable medium can also be distributed over network-coupled computer systems so that the computer readable code is stored and executed in a distributed fashion.

In the foregoing detailed description, reference was made to the accompanying drawings, which form a part of the description and in which are shown, by way of illustration, specific embodiments in accordance with the described embodiments. Although these embodiments are described in sufficient detail to enable one skilled in the art to practice the described embodiments, it is understood that these examples are not limiting; such that other embodiments may be used, and changes may be made without departing from the spirit and scope of the described embodiments.

Further, the foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of specific embodiments are presented for purposes of illustration and description. The description of and examples disclosed with respect to the embodiments presented in the foregoing description are provided solely to add context and aid in the understanding of the described embodiments. The description is not intended to be exhaustive or to limit the described embodiments to the precise forms disclosed. It will be apparent to one of ordinary skill in the art that many modifications, alternative applications, and variations are possible in view of the above teachings. In this regard, one of ordinary skill in the art will readily appreciate that the described embodiments may be practiced without some or all of these specific details. Further, in some instances, well known process steps have not been described in detail in order to avoid unnecessarily obscuring the described embodiments.

What is claimed is:

1. A wireless communication device comprising:
   a processor;
   a first radio comprising a first coexistence management controller, the first radio being coupled to the processor via an interface between the processor and the first radio; and
   a second radio comprising a second coexistence management controller, the second radio being coupled to the first radio via a second interface between the first radio and the second radio, wherein:
     the processor is configured to define a coexistence policy for the first radio and the second radio and to provide the coexistence policy to the first coexistence management controller via the interface between the processor and the first radio;
     the second radio is configured to provide state information of the second radio to the first radio via the second interface between the first radio and the second radio; and
     the first coexistence management controller is configured to use the state information of the second radio provided by the second radio to control operation of the first radio in accordance with the coexistence policy to mitigate interference with the second radio, wherein the state information of the second radio is provided to the first radio more frequently than the coexistence policy is provided to the first radio by the processor.

2. The wireless communication device of claim 1, wherein the state information of the second radio comprises an indication of an interference condition experienced by the second radio, and wherein the indication of the interference condition is determined by a radio measurement made by the second radio.

3. The wireless communication device of claim 1, wherein the state information of the second radio comprises an operating state indicative of whether the second radio is receiving or transmitting data during a time period.

4. The wireless communication device of claim 1, wherein the coexistence policy defines a priority between the first radio and the second radio.

5. The wireless communication device of claim 1, wherein the first radio implements a cellular communication technology, and wherein the second radio implements one or more of a wireless local area network (WLAN) communication technology or a wireless personal area network (WPAN) communication technology.

6. The wireless communication device of claim 1, wherein the processor is further configured to:
determine corresponding use case information based on active applications;
leverage knowledge of states of the active applications to derive a global view of wireless communication device usage and determine a use case context for the wireless communication device; and
define the coexistence policy based at least in part on the determined use case context, wherein a different coexistence policy is defined for a first use case context than for a second use case context.

7. The wireless communication device of claim 6, wherein the coexistence policy defines one or more priorities between the first radio and the second radio given the determined use case context.

8. The wireless communication device of claim 1, wherein:
the processor is further configured to provide the coexistence policy to the second coexistence management controller via a third interface between the processor and the second radio;
the first radio is further configured to provide state information of the first radio to the second radio via the second interface between the first radio and the second radio; and
the second coexistence management controller is configured to use the state information of the first radio provided by the first radio to control operation of the second radio in accordance with the coexistence policy,
wherein the state information of the first radio is provided to the second radio more frequently than the coexistence policy is provided to the second radio by the processor.

9. The wireless communication device of claim 1, wherein the first coexistence management controller is configured to use the state information of the second radio to control operation of the first radio in accordance with the coexistence policy at least in part by modifying filtering applied to a transmission by the first radio.

10. The wireless communication device of claim 1, wherein the first coexistence management controller is further configured to use radio measurements made by the first radio to further control operation of the first radio in accordance with the coexistence policy in order to mitigate interference with the second radio.

11. The wireless communication device of claim 1, wherein the first coexistence management controller is configured to adjust linearity of RF components of the first radio to mitigate effects of intermodulation distortion and/or harmonic distortion interference with the second radio.

12. A method for facilitating coexistence between wireless communication technologies on a wireless communication device that includes a processor, a first radio, and a second radio, the method comprising:
defining, by the processor, a coexistence policy for the first radio and the second radio;
providing, by the processor, the coexistence policy to a first coexistence management controller of the first radio via an interface between the processor and the first radio;
providing, by the second radio, state information of the second radio to the first radio via a second interface between the first radio and the second radio; and
using, by the first coexistence management controller of the first radio, the state information of the second radio to control operation of the first radio in accordance with the coexistence policy,
wherein the state information of the second radio is provided to the first radio more frequently than the coexistence policy is provided to the first radio by the processor.

13. The method of claim 12, wherein the state information of the second radio comprises one or more of an indication of an interference condition experienced by the second radio or an operating state indicative of whether the second radio is receiving or transmitting data during a time period.

14. The method of claim 12, wherein the coexistence policy prioritizes the second radio over the first radio, and wherein the first coexistence management controller of the first radio uses the state information of the second radio to control operation of the first radio by at least using the state information of the second radio to control data transmission by the first radio to mitigate interference with data reception by the second radio.

15. The method of claim 12, wherein the first radio implements a cellular communication technology, and wherein the second radio implements a wireless communication technology using an Industrial, Scientific, and Medical (ISM) band.

16. The method of claim 12, further comprising: by the processor:
determining a use case context of the wireless communication device; and
defining the coexistence policy based at least in part on the determined use case context, wherein a different coexistence policy is defined for a first use case context than for a second use case context.

17. The method of claim 12, further comprising:
providing, by the processor, the coexistence policy to a second coexistence management controller on the second radio via a third interface between the processor and the second radio; and
controlling operation of the second radio, by the coexistence management controller of the second radio, in accordance with the coexistence policy.

18. The method of claim 17, further comprising:
providing, by the first radio, state information of the first radio to the second radio via the second interface between the first radio and the second radio; and
using the state information of the first radio provided by the first radio, by the second coexistence management controller of the second radio, to control operation of the second radio in accordance with the coexistence policy.

19. A method for facilitating coexistence between wireless communication technologies on a wireless communication device, the method comprising:

by a processor:

defining a coexistence policy for a first radio and a second radio co-located on the wireless communication device; and providing the coexistence policy to the first radio via an interface between the processor and the first radio to configure a first coexistence management controller on the first radio to control operation of the first radio in accordance with the coexistence policy based at least in part on state information of the first radio provided to the first radio by the second radio via a second interface between the first radio and the second radio, wherein the state information of the second radio is provided to the first radio more frequently than the coexistence policy is provided to the first radio by the processor.

20. The method of claim 19, further comprising:

by the processor:

determining a use case context of the wireless communication device; and defining the coexistence policy based at least in part on the determined use case context, wherein a different coexistence policy is defined for a first use case context than for a second use case context.

* * * * *